United States Patent
Watson (10) Patent No.: US 8,020,575 B1
(45) Date of Patent: Sep. 20, 2011

(54) WATER LINE TAPPING METHOD

(76) Inventor: Gerald D. Watson, El Dorado, KS (US)

( * ) Notice: Subject to any disclaimer, the term of this patent is extended or adjusted under 35 U.S.C. 154(b) by 275 days.

(21) Appl. No.: 12/419,863

(22) Filed: Apr. 7, 2009

(51) Int. Cl.
*F16K 43/00* (2006.01)
*B23B 41/08* (2006.01)

(52) U.S. Cl. .................. 137/15.16; 137/15.13; 137/317; 137/318; 137/364

(58) Field of Classification Search .................. 137/318, 137/315.06, 15.16, 15.12, 15.13, 301, 15.03, 137/364, 317; 73/201, 273; 285/30
See application file for complete search history.

(56) References Cited

U.S. PATENT DOCUMENTS

| | | | | |
|---|---|---|---|---|
| 2,018,615 A * | 10/1935 | Lofton | ............................ | 73/201 |
| 3,935,736 A * | 2/1976 | Enright | ............................ | 73/201 |
| 4,140,155 A * | 2/1979 | Tannery | ......................... | 137/318 |
| 4,305,282 A * | 12/1981 | Hunt | ................................ | 73/201 |
| 6,286,542 B1 * | 9/2001 | Morain et al. | ................. | 137/318 |
| 6,820,646 B2 * | 11/2004 | Helle | ............................ | 137/364 |
| 7,281,545 B2 * | 10/2007 | Hunt | ......................... | 137/315.06 |

* cited by examiner

*Primary Examiner* — Kevin Lee
(74) *Attorney, Agent, or Firm* — Kenneth H. Jack; Davis & Jack, L.L.C.

(57) ABSTRACT

A method for tapping a water line, the water line being buried below a subterranean frost line, the water line traversing a water meter box's lower end, and having first and second sections within the water meter box respectively extending upwardly to and extending downwardly from a water meter, the method for tapping the water line including steps of providing a flexible tube having an intake end and an output end, the flexible tube having a length sufficient for, upon attachment of the flexible tube's intake end to the water line within the water meter box, extensions and retractions of the flexible tube between first and second positions, the flexible tube's output end residing below the subterranean frost line while in the first position and the flexible tube's output end extending upwardly from the water meter box while in the second position; attaching the flexible tube's intake end to the water line within the water meter box; providing a spigot and attaching the spigot to the flexible tube's output end; providing a mounting bracket for releasably holding the spigot within the water meter box; and performing further steps of grasping the spigot, releasing the spigot from the mounting means, raising the spigot and the flexible tube's output end to the second position, opening the spigot for emission of water sample, closing the spigot, and lowering the spigot and the flexible tube's output end to the first position.

11 Claims, 7 Drawing Sheets

WATER LINE TAPPING METHOD

FIELD OF THE INVENTION

This invention relates to methods and processes for monitoring and maintaining the potability of water within distribution systems which include a network of water lines. More particularly, this invention relates to such methods and processes which extract or tap, for testing purposes, sample portions of water from water lines within such systems.

BACKGROUND OF THE INVENTION

In order to monitor and properly maintain the potability of water within the buried water lines of a municipal or rural water distribution network, operators of such networks are commonly required by public health agency regulations to periodically retrieve and test samples of water from water lines at various locations throughout the water distribution system. Upon such water retrieval and sampling, the water system operator or a water testing laboratory typically tests the water samples for appropriate chlorine levels and/or the presence of pathogens and contaminants.

One of the problems confronting water system operators in retrieving such needed water samples arises where sampling must occur at residential water usage sites. In many such cases, water from a residence's household water spigots is not available to the operator at a particular time the operator arrives at the residence to retrieve a sample. Also, in many cases, a residence's water outlets, faucets, and spigots are not suitable for sampling and testing due to utilization of a household water softening system.

Another potential location where a water system operator might obtain a needed water sample is the water pipe and meter components which are exposed within the residence's water meter box. However, water is typically not sampleable within such water meter box without performing burdensome steps of disconnecting and reconnecting water meter and water line couplings. Such water meter box means of water sampling is time consuming and is undesirably mechanically complex.

Another known method for achieving such needed water sampling provides a water spigot post which extends upwardly from ground level and from a buried water line. However, such spigot posts typically must have freeze protection and insulation and are undesirably expensive, difficult to install, and are subject to damage from accidental impacts with riding lawnmowers and the like.

The instant inventive method solves or ameliorates the water sampling problems and challenges discussed above by including structure providing steps, installation steps, and usage steps which allow water to be mechanically simply and economically sampled from a water meter box.

BRIEF SUMMARY OF THE INVENTION

The instant inventive method for tapping a water line is particularly applicable and performable in relation to water lines which are buried below a subterranean frost line, where the water is within a water meter box. Within such meter box, the water line typically presents first and second sections or connector segments which respectively extends upwardly from the horizontal run of the water line to a water meter and extends downwardly from the water meter to return to the water line's horizontal run. In a preferred embodiment of the instant invention, all of the structures provided in the steps of the method are stored within such water meter box at an elevation which underlies the area's cold weather subterranean frost line.

In the instant inventive method, a flexible tube is preferably provided. Such tube is preferably between ¼" inch and ½" in diameter, and preferably is externally clad within and protected by a braided sheath of corrosion resistant wire. Stainless steel clad tubing is preferred. The flexible tube is preferably fitted to a length which is sufficient to allow, upon attachment of an intake end of the tube to the water line within the water meter box, manual upward and downward extensions and retractions of such tube's output end between vertical first and second positions. In the first position the output end of the flexible tube preferably rests or is mounted within the water meter box at an elevation below the frost line. Upon movement to the second position, such output end is preferably raised by an operator to an elevation, preferably at least waist high, above the upper opening of the water meter box.

According to the instant inventive method, the lower intake end of the flexible tube is preferably attached in a "T" joint fashion to the water line within the water meter box so that water within the water line may communicate with and enter the tube. Such attachment step preferably includes a provision of a saddle valve which incorporates and utilizes a screw driven self-piercing or pipe piercing valve stem. Provision of such valved tube connection allows a water system operator to economically and mechanically efficiently retrofit a water line exposed within the water meter box for performance of the further steps of the instant inventive method.

A further structure providing step of the instant inventive method attaches a valved spigot to the upper output end of the flexible tube. Mounting means for releasably holding the spigot and its attached flexible tube output end within the water meter box and below the subterranean frost line are also preferably provided.

The water system operator performing the instant inventive method may initially access the interior of the water meter box, outfitted as described above, by removing the box's cover plate. Thereafter, the operator may reach downwardly into the box and may grasp the spigot, disengaging it from the provided mounting means. Thereafter, such operator may manually upwardly draw the spigot and the output end of the flexible tube from its lower first position below the frost line to its second position. Thereafter, the operator may open the spigot's valve to cause a flow of sample water to emit therefrom. Upon collection of such sample water, the operator may perform on-site chlorine level testing or may bottle the sample for laboratory testing for contaminants and pathogens. Following emission and collection of such sample water, the operator may, according to the instant inventive method, reclose the spigot and may downwardly return the spigot into the water meter box, re-engaging the spigot at the first position via the mounting means. The preferred sub-frost line elevation of such mounting means advantageously protects water remaining within the flexible tube from freeze damage, allowing the method to be repeatedly performed over a span of several years.

Accordingly, objects of the instant invention include the provision of and performance of structures and method steps in service of the beneficial functions as described above, and for overcoming and solving problems and deficiencies inherent in prior art sampling methods, as described above.

Other and further objects, benefits, and advantages of the present invention will become known to those skilled in the

DETAILED DESCRIPTION OF A PREFERRED EMBODIMENT

Figure 1:
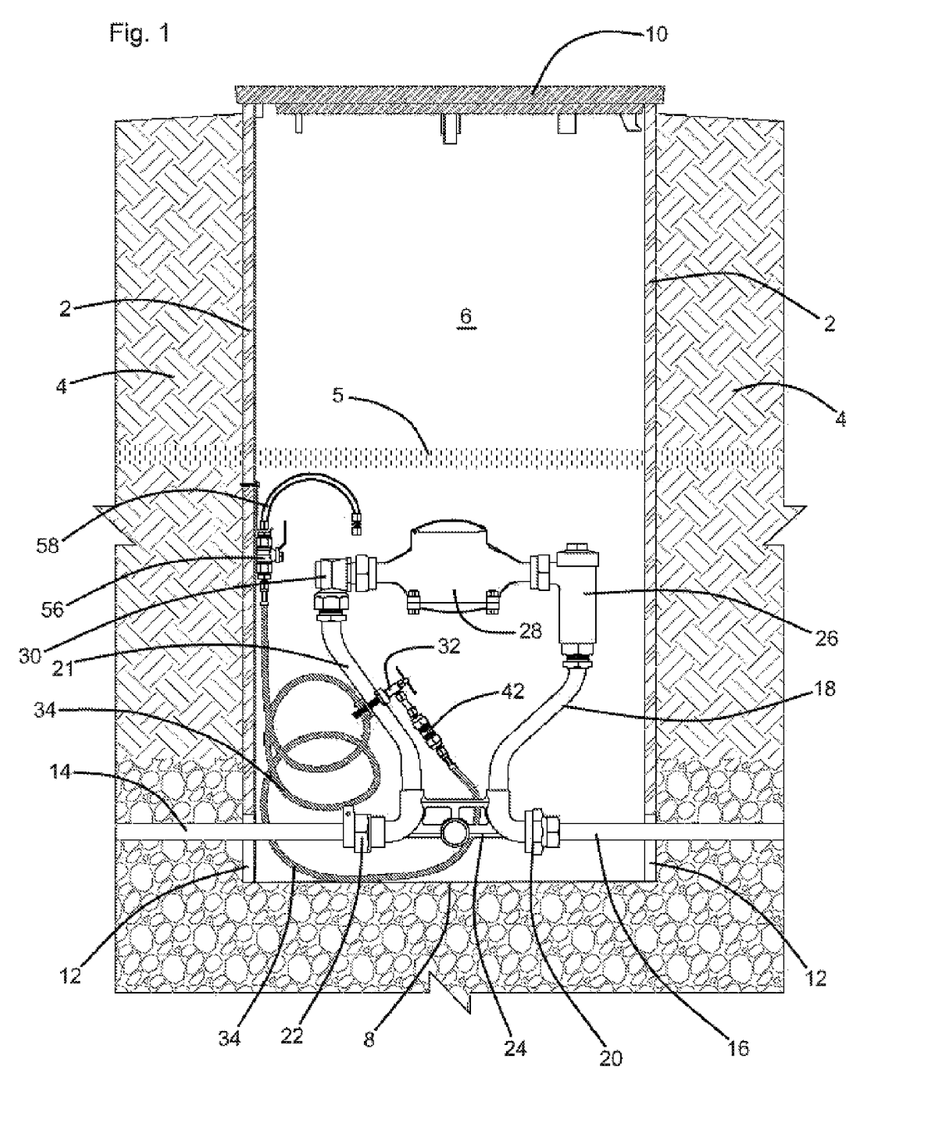
FIG. 1 is a inground vertical sectional view showing structures which are provided in performance of steps of the instant inventive method.

Referring now to the drawings, and in particular to FIG. 1, the ground 4 has a frost line represented by vertical dashes 5. Line 5 demarks a subterranean level below which freezing temperatures normally do not occur during cold weather months. A cylindrical (either circular or rectangular) water meter box 2 is buried within the earth 4, such box 2 having an upper opening covered by a fitted lid 10 and having an exposed lower opening 8. A horizontally extending water line 14 and 16 enters and exits the lower end of the interior 6 of the water meter box 4 through side wall slots or notches 12. Water entering the meter box 2 via line 14 flows into an upwardly extending line segment 21 for passage through a water meter 28. Such water exits the meter 28 to flow downwardly through line segment 18, then passing outwardly from the water meter box 2 through line 16. A line coupling support joint 20, 22, 24, interconnects lines 14 and 16 with line segments 21 and 18, and provides structural support for the water meter 28 within the box 2. An "L" coupling joint 30 interconnects the upper end of line segment 21 with the upstream end of the water meter 28, and an "L" configured shut off valve 26 couples the upper end of line segment 18 with the downstream end of the water meter 28.

Figure 2:
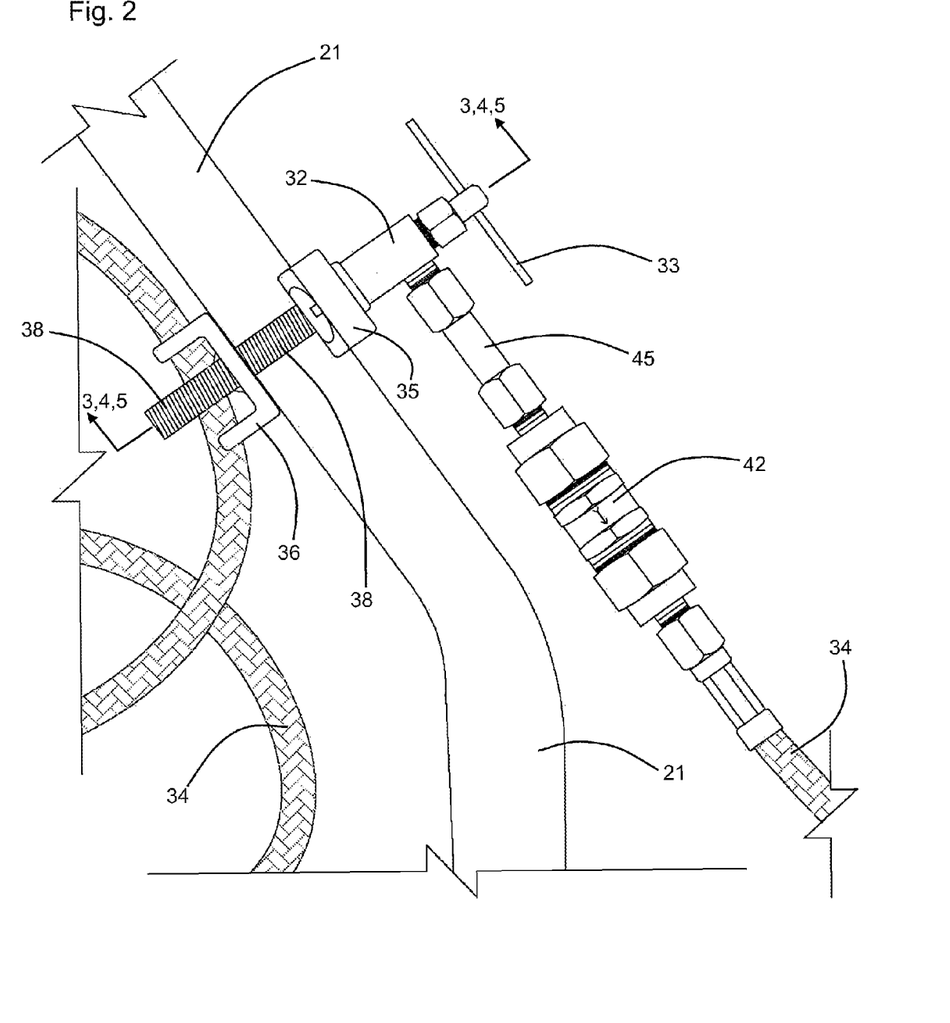
FIG. 2 is a magnified view of saddle valve connection components of the structures depicted in FIG. 1.
Figure 3:
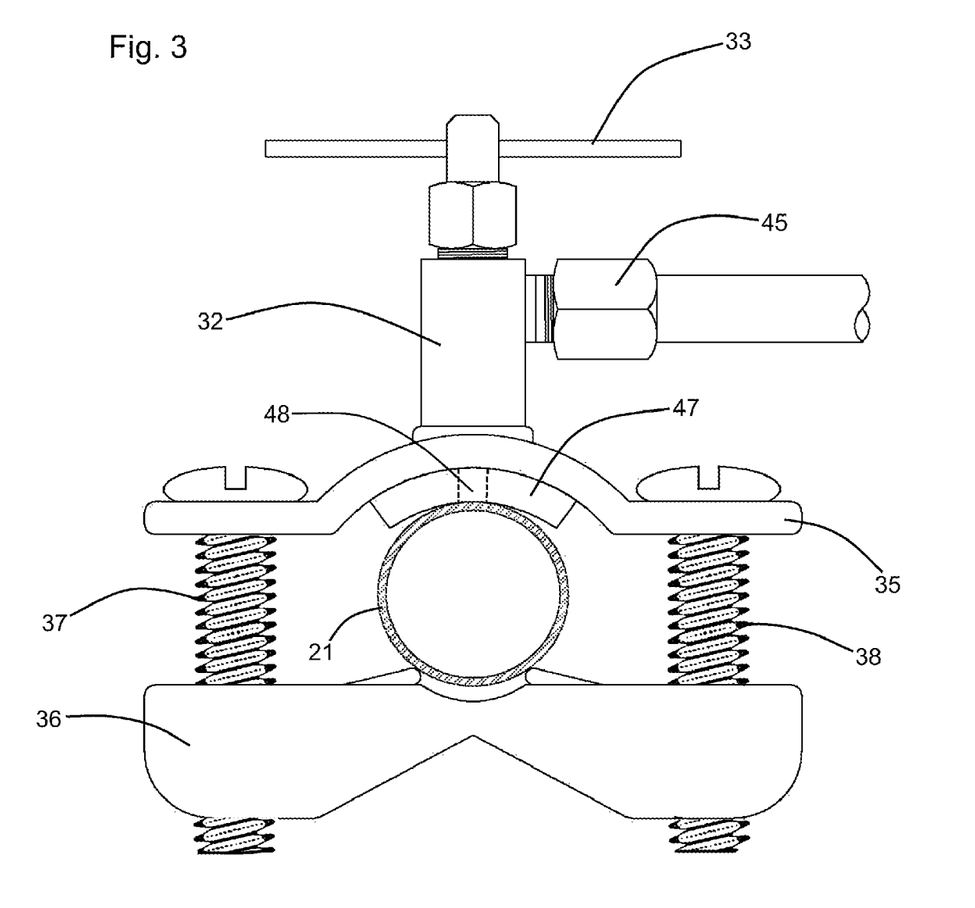
FIG. 3 is a sectional view as indicated in FIG. 2.
Figure 4:
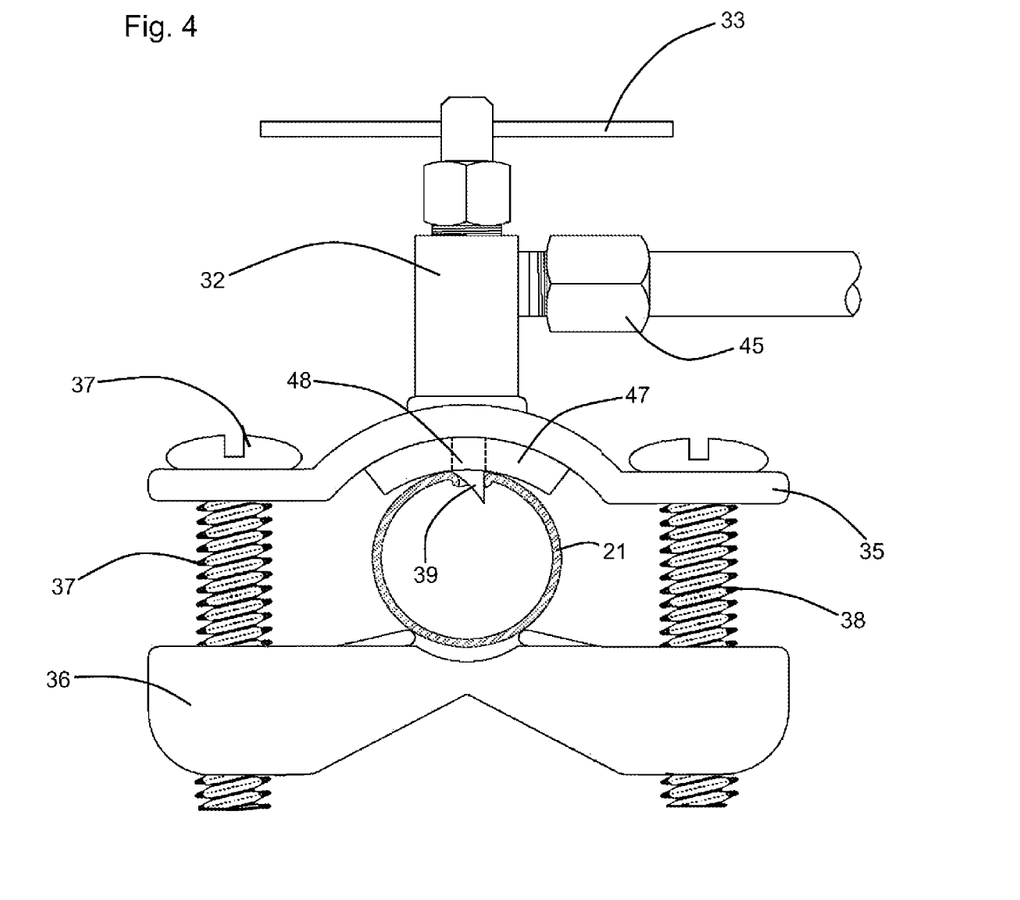
FIG. 4 is an alternatively configured sectional view as indicated in FIG. 2.
Figure 5:
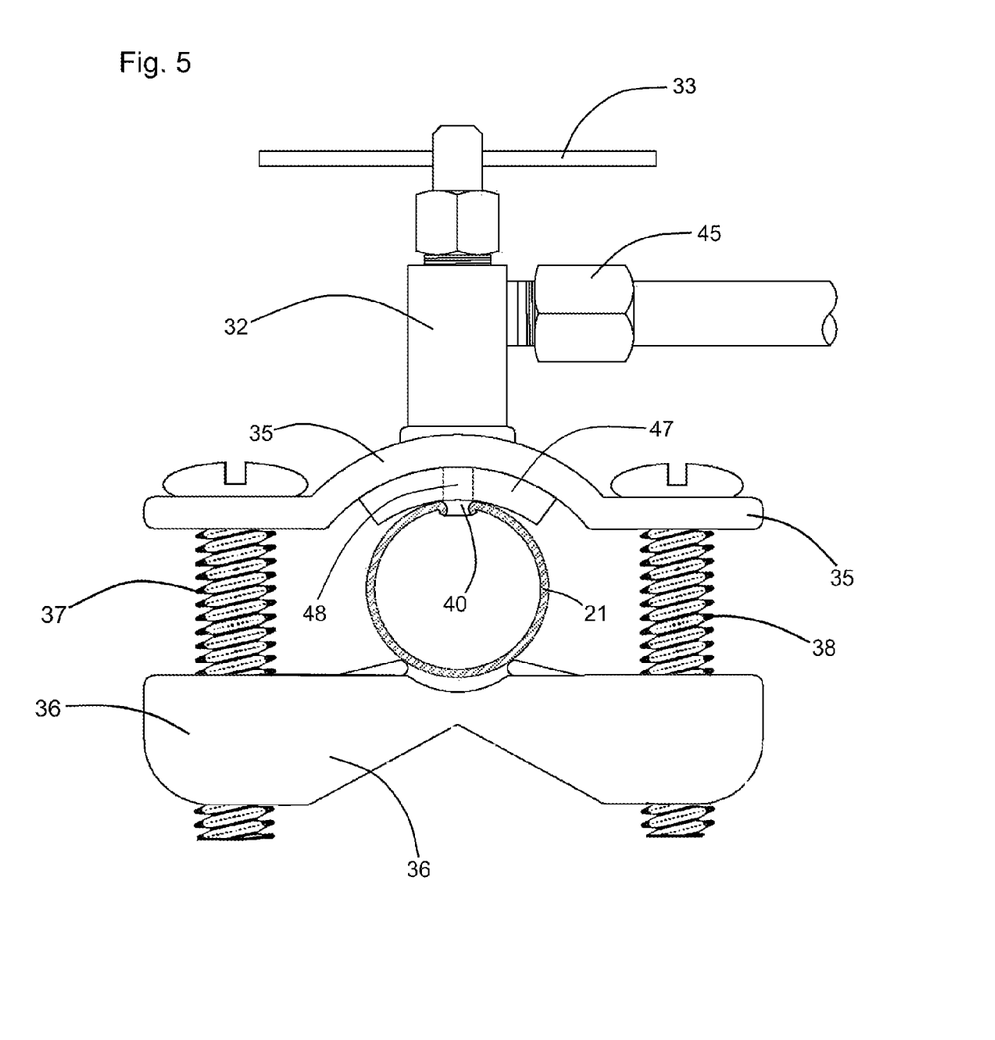
FIG. 5 is a further alternatively configured sectional view, as indicated in FIG. 2.

Referring simultaneously to FIGS. 1 and 2, a flexible tube 34 is preferably provided, such tube 34 preferably being clad within and protected by a corrosion stainless steel braided sheath for purposes of durability and longevity of the tube. The lower or intake end of the flexible tube 34 is preferably attached for water flow communication to one of the vertically extending line segments 18 or 21 of the water line. Referring further simultaneously to FIG. 3, a saddle valve 32 is preferably provided for economically and mechanically simply achieving such water flow communicating tube end attachment. In order to install the saddle valve 32 upon one of the line segments (for example segment 21 as depicted), an operator may initially threadedly withdraw screws 37 and 38 from the valve's lower saddle bracket 36. Thereafter, the line segment 21 may be received between screws 37 and 38 so that the outer wall of the line segment 21 rests against an elastomeric water sealing element 47 which is held by the valve's opposing saddle bracket 35. Thereafter, the lower saddle bracket 36 may be threadedly re-engaged with screws 37 and 38, such screws being tightened until the line segment 21 is securely held between the compressed seal 27 and the lower saddle bracket 36. Referring further simultaneously to FIG. 4, the saddle valve 32 preferably incorporates a screw driven pipe piercing valve stem 39. Upon manual clockwise turning of a "T" configured thumb turn 33, the valve 32 drives the sharpened lower end of the pipe piercing valve stem 39 downwardly through an aperture 48 within the seal 47, to impinge against the outer surface of the line segment 21. Continued turning of the thumb turn 33 advantageously causes the stem 39 to pierce or puncture the line segment 21. Upon opposite turning of thumb turn 33 for upward withdrawal of the pipe piercing valve stem 39, an outlet port 40 for communicating a flow of water from the line 21 to the flexible tube 34 is formed. Referring in particular to FIG. 2, a back flow checking valve 42 is preferably installed and interposed between the intake end of the flexible tube 34 and the saddle valve 32, the upstream end of the back flow checking valve 42 being coupled with the saddle valve 32 by a coupling member 45. While the provision of a saddle valve 32 constitutes a preferred means for achieving water flow from the water line segment 21 to the flexible tube 34, provisions of other commonly known fluid communicating joints are considered to be method steps falling within the scope of the invention.

Figure 6:
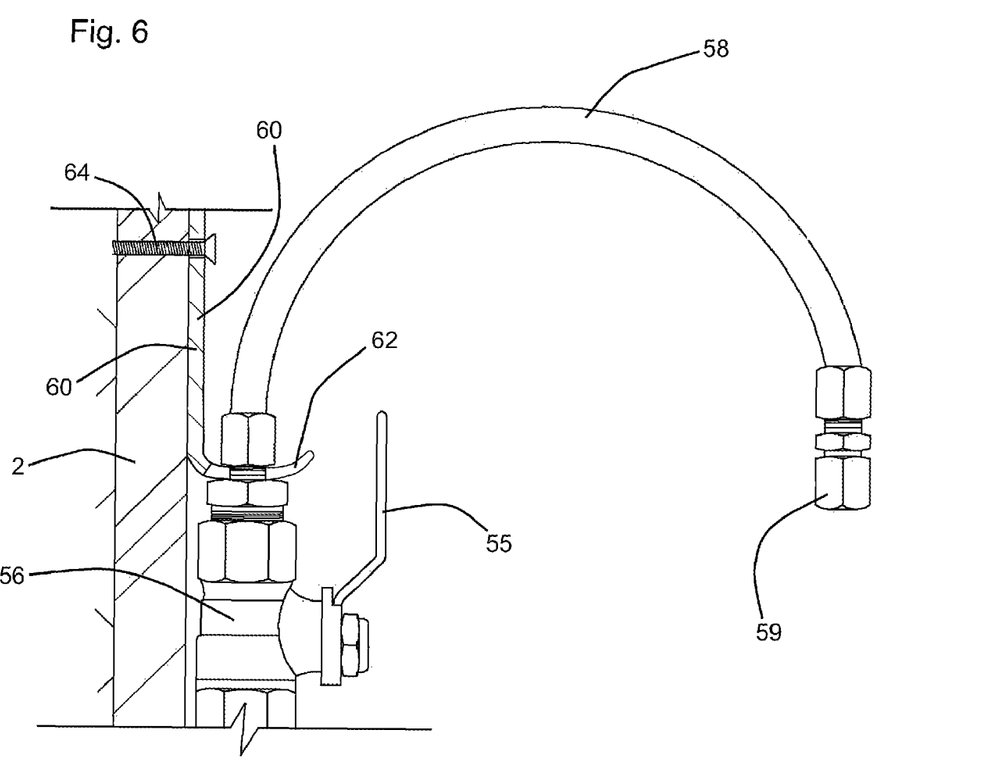
FIG. 6 is an alternative magnified view of valved spigot components of the structures depicted in FIG. 1.

Referring simultaneously to FIGS. 1 and 6, a spigot 58 is preferably attached for water flow communication to the outlet end of the flexible tube 34. The spigot 58 preferably comprises a shut off ball valve 56 which is manually openable and closable by a turn lever 55. The distal or outlet end of the spigot 58 preferably is covered by a removable cap 59 to prevent insects and debris from entering the interior of the spigot while the spigot is stored and is not in use.

Referring further simultaneously to FIGS. 1 and 6, mounting means are preferably provided in order to allow the spigot 58 to be stored when not in use within the interior 6 of the water meter box 2, such storage preferably being at a position below the frost line 5. A forked mounting bracket 60 having a pair of spigot receiving and supporting tines 62 may suitably serve as the releasable mounting means, such bracket 60 being affixed to the interior side wall of the water meter box 2 by a screw 64. Alternatively, or in addition to such bracket 60 releasable mounting means, configuration of the distal end of the spigot 58 to function as a hook (as is depicted) may suitably serve as the releasable mounting means. For purposes of storage while not in use, such curved hook portion of the spigot may suitably be caused to overlie, rest against, and be supported by the water meter 28, the "L" joint 30 or the valve 26.

Figure 7:
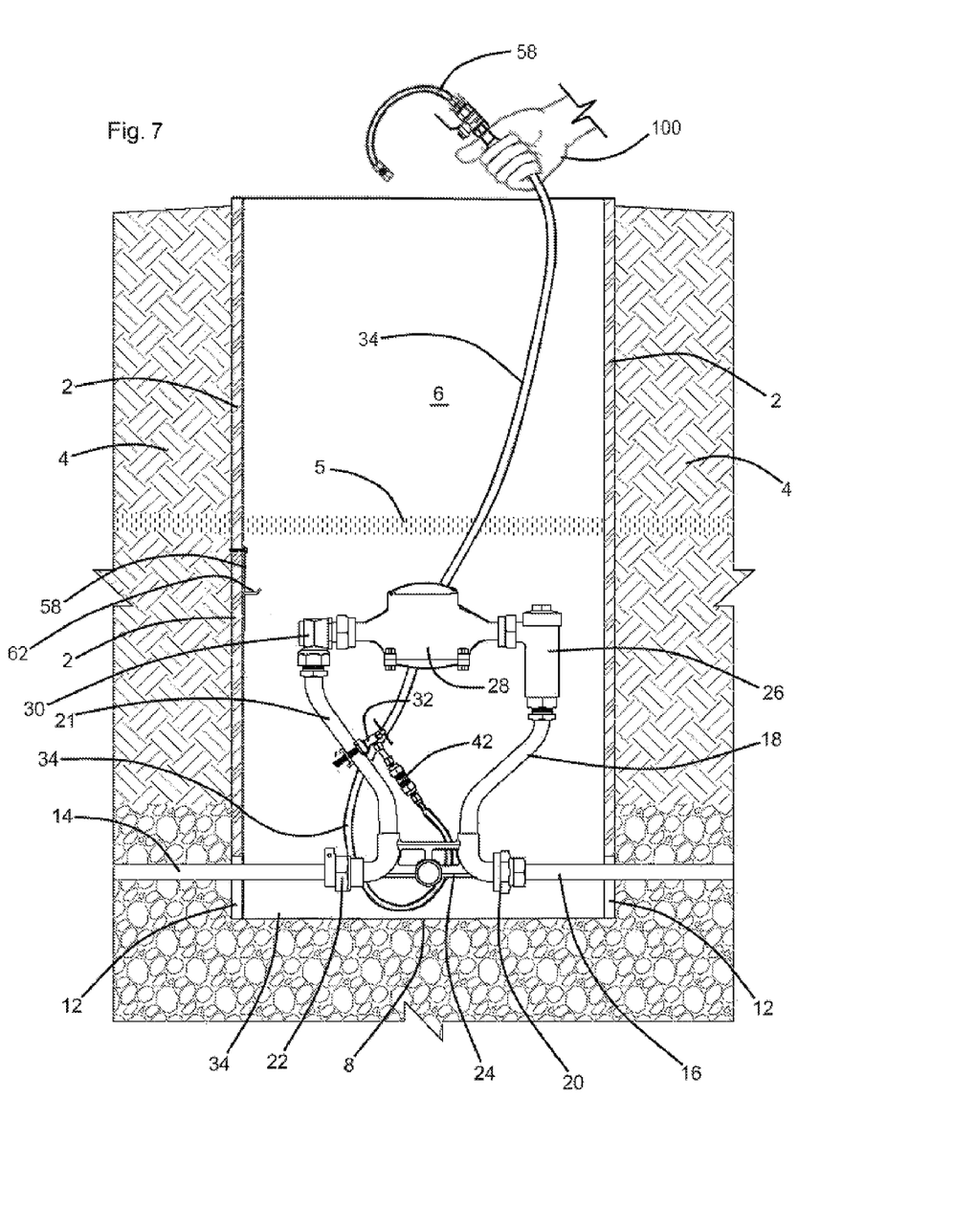
FIG. 7 redepicts FIG. 1, the view showing a spigot raised above a frost line 5 by a user.

Referring to FIG. 1, the flexible tube 34 is preferably sized and fitted so that, upon attachment of such tube's intake end as depicted in FIG. 1 to line segment 21, the outlet end of the flexible tube 34 and the spigot 58 may be manually vertically raised between first and second positions. In the first position, the spigot 58 is held below the frost line 5 as depicted in FIG. 1. Referring further to FIG. 7, in the second position, upon removal of lid 10, the spigot 58 is raised by the operator's hand 100 to an elevation above the frost line 5 and overlying the upper opening of the water meter box 2. Preferably, the flexible tube 34 has sufficient length to allow the operator to comfortably hold the spigot 58 while standing on the ground surface near the water meter box.

In further performance of the steps of the instant inventive method, referring simultaneously to FIGS. 1 and 6, the operator may initially remove lid 10 from the upper opening of the water meter box 2. Thereafter, the operator may reach into the interior 6 of the water meter box 2 and may grasp the spigot 58 to disengage it from the support tines 62 of the bracket 60. Thereafter, the operator may draw the spigot 58 upwardly through the interior 6 until the spigot 58 is raised to a convenient elevation, the flexible tube 34 uncoiling and trailing after the spigot 58 during elevation. Thereafter, the operator may threadedly remove cap 59 and may turn handle 55 to open the ball valve 56. Upon performance of such manipulations, water from line segment 21 commences to flow into and through the saddle valve 32, thence through the back flow checking valve 42, thence into and through the flexible tube 34, to emit from the distal outlet end of the spigot 58. Such emitted water may be collected by the operator for on-site testing for chlorine levels or contaminants or may be collected as bottled water samples for submission to a testing laboratory. Thereafter, the operator may close the valve 56 and may reinstall the cap 59. Thereafter, the operator may downwardly return the spigot 58 and the outlet end of the flexible tube 34 into the interior 6 of the water meter box 2 and may re-engage the spigot 58 with the mounting bracket 60. At such remounted location, any water retained within the spigot 58 or within the flexible tube 34 remains below the frost line 5 advantageously preventing freezing and structural damage. Alternatively, the operator may store the spigot below the frost line by hooking the spigot 58 over the water meter 28 or one of its upstream or downstream coupling members.

While the principles of the invention have been made clear in the above illustrative embodiment, those skilled in the art may make modifications in the method steps of the invention without departing from those principles. Accordingly, it is intended that the description and drawings be interpreted as illustrative and not in the limiting sense, and that the invention be given a scope commensurate with the appended claims.

I claim:

1. A method for tapping a water line, the water line being buried below a subterranean frost line, the water line traversing a water meter box's lower end, and having first and second sections within the water meter box respectively extending upwardly to and extending downwardly from a water meter, the method for tapping the water line comprising steps of:
    (a) providing a flexible tube having an intake end and an output end, the flexible tube having a length sufficient for, upon attachment of the flexible tube's intake end to the water line within the water meter box, extensions and retractions of the flexible tube between first and second positions, the flexible tube's output end residing below the subterranean frost line while in the first position and the flexible tube's output end extending upwardly from the water meter box while in the second position;
    (b) attaching the flexible tube's intake end to the water line within the water meter box;
    (c) providing a spigot and attaching the spigot to the flexible tube's output end;
    (d) providing mounting means for releasably holding the spigot within the water meter box, and, upon said releasable holding;
    (e) performing further steps of grasping the spigot, releasing the spigot from the mounting means, raising the spigot and the flexible tube's output end to the second position, opening the spigot for emission of water, closing the spigot, and lowering the spigot and the flexible tube's output end to the first position.

2. The method of claim 1 wherein the flexible tube intake end attaching step positions the flexible tube's intake end at the water line's first section or at the water line's second section.

3. The method of claim 2 wherein the flexible tube intake end attaching step further comprises providing a saddle valve having a screw actuatable pipe piercing valve stem, mounting the saddle valve at the flexible tube intake end attaching step position, and actuating the pipe piercing valve stem to puncture the water line.

4. The method of claim 3 further comprising providing a back flow checking valve, and interposing said valve for fluid communication between the saddle valve and the flexible tube's intake end.

5. The method of claim 4 wherein the flexible tube providing step includes provision of metal braid tube sheathing.

6. The method of claim 5 wherein the mounting means providing step configures an output end of the spigot to function as a water meter engaging hook.

7. The method of claim 5 wherein the mounting means providing step provides a box wall mounted spigot receiving bracket.

8. The method of claim 7 wherein the box wall mounted spigot receiving bracket providing step attaches the spigot receiving bracket below the subterranean frost line.

9. The method of claim 1 wherein the spigot providing step comprises providing a valve at a spigot intake end.

10. The method of claim 9 wherein the spigot providing step configures a spigot output end as a water meter engaging hook.

11. The method of claim 10 wherein the spigot providing step provides a removable cap over the spigot's output end.

* * * * *